(12) United States Patent
Astsaturov et al.

(10) Patent No.: US 9,993,458 B2
(45) Date of Patent: Jun. 12, 2018

(54) METHOD OF TREATING MYC-AMPLIFIED TUMORS WITH RNA-POLYMERASE II INHIBITORS

(71) Applicant: Institute for Cancer Research, Philadelphia, PA (US)

(72) Inventors: Igor Astsaturov, Philadelphia, PA (US); Vladimir Khazak, Philadelphia, PA (US); Ilya Serebriiski, Philadelphia, PA (US)

(73) Assignees: Institute For Cancer Research, Philadelphia, PA (US); NexusPharma, Inc., Langhorne, PA (US)

( * ) Notice: Subject to any disclaimer, the term of this patent is extended or adjusted under 35 U.S.C. 154(b) by 0 days. days.

(21) Appl. No.: 15/242,675

(22) Filed: Aug. 22, 2016

(65) Prior Publication Data
US 2016/0354339 A1    Dec. 8, 2016

Related U.S. Application Data (63) Continuation of application No. PCT/US2015/016504, filed on Feb. 19, 2015.

(60) Provisional application No. 61/942,650, filed on Feb. 21, 2014.

(51) Int. Cl.
| | |
|---|---|
| *A61K 31/365* | (2006.01) |
| *A61K 31/4184* | (2006.01) |
| *C12Q 1/68* | (2018.01) |
| *G01N 33/574* | (2006.01) |

(Continued)

(52) U.S. Cl.
CPC ........ *A61K 31/365* (2013.01); *A61K 31/4184* (2013.01); *A61K 45/06* (2013.01); *C07D 493/22* (2013.01); *C12Q 1/6886* (2013.01); *G01N 33/574* (2013.01); *G01N 33/57438* (2013.01); *G01N 33/57496* (2013.01);

(Continued)

(58) Field of Classification Search
CPC .. A61K 31/365; A61K 31/4184; A61K 45/06; C07D 493/22; C12Q 1/6886; C12Q 2600/106; C12Q 2600/158; G01N 2333/4703; G01N 33/574; G01N 33/57438; G01N 33/57496
See application file for complete search history.

(56) References Cited

U.S. PATENT DOCUMENTS

| | | |
|---|---|---|
| 6,150,539 A | 11/2000 | Musser |
| 6,548,537 B1 | 4/2003 | Dai et al. |
| 7,863,464 B2 | 1/2011 | Yuan et al. |

(Continued)

OTHER PUBLICATIONS

Nesbit et al. (Oncogene 1999, 18, pp. 3004-3016.*

(Continued)

*Primary Examiner* — Savitha M Rao
(74) *Attorney, Agent, or Firm* — Stradley Ronon Stevens & Young, LLP (57) ABSTRACT

Systems and methods for determining whether a cancer patient may respond to inhibition of RNA polymerase II as a treatment for the patient are provided. Inhibition of RNA polymerase II may be by way of chemotherapy with an agent such as triptolide, an analog of triptolide, or a prodrug form of triptolide. The cancer patient may be a pancreatic cancer patient, an ovarian cancer patient, a gastric cancer patient, or an esophageal cancer patient. The patient may have any cancer in which c-Myc is over-expressed or over-amplified.

5 Claims, 6 Drawing Sheets

(51) Int. Cl.
*A61K 45/06* (2006.01)
*C07D 493/22* (2006.01)
(52) U.S. Cl.
CPC . *C12Q 2600/106* (2013.01); *C12Q 2600/158* (2013.01); *G01N 2333/4703* (2013.01)

(56) References Cited

U.S. PATENT DOCUMENTS

| | | |
|---|---|---|
| 2012/0040842 A1 | 2/2012 | Baker et al. |
| 2012/0302629 A1* | 11/2012 | Wang .................. C12Q 1/6886 514/449 |
| 2014/0107077 A1 | 4/2014 | Georg et al. |

OTHER PUBLICATIONS

Manzo et al. (Cancer Research, Oct. 2012, vol. 72 (20) pp. 5363-5373.*
Titov et al. (Nat Chem Biol. Mar. 2011,; 7(3) pp. 182-188).*
Bodoky et al. (Invest. New Drugs (2012) 30: 1216-1223).*
Beyer et al. (Pancreas, vol. 40 (8) 2011, pp. 1308-1366).*
Cui et al., "Genetically Defined Subsets of Human Pancreatic Cancer Show Unique In Vitro Chemosensitivity", Clin Cancer Res, 2011, vol. 7, No. 3, pp. 182-188.
Huang et al., "Triptolide Inhibits MDM2 and Induces Apoptosis in Acute Lymphoblastic Leukemia Cells through a p53-Independent Pathway", Mol Cancer Ther, 2013, vol. 12, No. 2, pp. 184-194.
Manzo et al., "Natural Product Triptolide Mediates Cancer Cell Death by Triggering CDK7-Dependent Degradation of RNA Polymerase II", Cancer Research, 2012, vol. 72 (20), pp. 5363-5373.

* cited by examiner

METHOD OF TREATING MYC-AMPLIFIED TUMORS WITH RNA-POLYMERASE II INHIBITORS

CROSS REFERENCE TO RELATED APPLICATIONS

This application is a continuation of PCT International Application No. PCT/US15/016504, which was filed on Feb. 19, 2015, and claims priority to U.S. Provisional Patent Application No. 61/942,650, which was filed on Feb. 21, 2014. The contents of each application are incorporated by reference herein, in their entirety and for all purposes.

FIELD OF THE INVENTION

The invention relates generally to the field of cancer treatment. More particularly, the invention relates to systems and methods for assessing whether a tumor over-expresses or over-amplifies c-Myc and, if it does, inhibiting the biologic activity of RNA polymerase II (pol II) in cells of the tumor in order to inhibit tumor growth; c-Myc over amplification and over-expression serves as a biomarker for inhibiting tumor growth by inhibiting RNA pol II.

BACKGROUND OF THE INVENTION

Various publications, including patents, published applications, technical articles and scholarly articles are cited throughout the specification. Each of these cited publications is incorporated by reference, in its entirety and for all purposes, in this document.

Pancreatic ductal adenocarcinoma (PDAC) affects 44,000 individuals yearly in the United States. Almost universally, this cancer is lethal, with very limited efficacy of chemotherapy (gemcitabine, nab-paclitaxel, platinum, 5FU). Clinical trials addressing this glaring need for expanded portfolio of anti-cancer agents active in PDAC have been unsuccessful, and a lack of active agents has blocked progress in improving survival rates for pancreatic cancer. Transformative new therapies are urgently needed for this devastating malignancy, which is understood to be nearly universally driven by "undruggable" and interdependent mutations in KRAS, P53 and MYC.

Oncogenic MYC is amplified in from 8% to as high as 30% of PDAC. MYC expression is directly regulated by multiple KRAS effectors, so that phosphorylation of Serine-62 by ERK stabilizes MYC, whereas subsequent phosphorylation of Threonine-58 by GSK3b (which is inhibited by AKT) is required for MYC ubiquitin-mediated degradation. In addition to MYC's ability to function as a bHLH transcriptional factor, MYC causes transcription amplification. Tumors expressing high MYC levels show increased levels of MYC in the promoter regions of actively transcribed genes. Frequent amplification of c-Myc in human cancers has been the focus of investigation, but it is believed that no effective way to curtail viability of c-Myc-dependent cancers has yet been uncovered.

Mechanistically, suppressing MYC necessitates shutting down the pre-existing oncogenic transcriptional program including the MYC gene itself. This is achievable through interference with various components of RNA Pol II complex. The choice of anti-MYC targets, however, remains limited.

SUMMARY OF THE INVENTION

A system for determining the sensitivity of a tumor to RNA polymerase II inhibition comprises a data structure comprising reference values for a level of c-Myc mRNA, a level of c-MYC protein, or both a level of c-Myc mRNA and a level of c-MYC protein corresponding to a degree of sensitivity of a tumor to treatment with an agent that inhibits the biologic activity of RNA polymerase II and a processor operably connected to the data structure. The processor is preferably programmed to compare a level of c-Myc mRNA, a level of c-MYC protein, or a level of both c-Myc mRNA and c-MYC protein determined from a subject with the reference values for the level of c-Myc mRNA, level of c-Myc protein, or both the level of c-Myc mRNA and c-MYC protein in the data structure, and also programmed to determine a RNA polymerase II inhibition sensitivity score as a result of the comparison. The system may comprise computer readable media comprising executable code for causing the processor to compare the level of c-Myc mRNA, the level of c-MYC protein, or the level of both c-Myc mRNA and c-MYC protein determined from the cell isolated from the tumor with the reference values, and executable code for causing the processor to determine a RNA polymerase II inhibition sensitivity score as a result of the comparison.

The RNA polymerase II inhibition sensitivity score preferably comprises a likelihood that the agent will or will not inhibit the biologic activity of RNA polymerase II in the tumor, thereby treating the tumor. Sensitivity includes killing of tumor cells. The degree of sensitivity may take into account whether the tumor cells are resistant to the agent or particular doses of the agent.

The agent may inhibit the expression or the biologic activity of the excision repair cross-complementing rodent repair deficiency, complementation group 3 (ERCC3) protein. The agent may inhibit the transcription of the ERCC3 gene. The agent may inhibit the translation of ERCC3 mRNA. The agent may inhibit the biologic activity of the ERCC3 protein. The agent may inhibit the transcription of the c-Myc gene. The agent may inhibit the expression of the C-MYC protein. The agent may inhibit the interaction of the ERCC3 protein with the C-MYC protein. The agent may inhibit the KRAS-ERK-MYC signal cascade. The agent may induce degradation of RNA polymerase II. The agent may induce proteasome degradation of RNA polymerase II. The agent may comprise triptolide, an analog of triptolide, or a prodrug form of triptolide.

The tumor may comprise cells that over-amplify c-Myc mRNA. The tumor may comprise cells that over-express the c-Myc protein. In some preferred aspects, the tumor comprises a tumor of the pancreas. A non-limiting example of a pancreatic tumor is pancreatic ductal adenocarcinoma (PDAC). In some preferred aspects, the tumor comprise a tumor of the ovaries. In some preferred aspects, the tumor comprises a tumor of the stomach. In some preferred aspects, the tumor comprises a tumor of the esophagus.

A method for treating a tumor in a subject in need thereof comprises comparing the level of c-Myc mRNA, the level of c-MYC protein, or the level of both c-Myc mRNA and c-MYC protein determined from a cell isolated from the tumor with reference values for a level of c-Myc mRNA, c-MYC protein, or both c-Myc mRNA and c-MYC protein corresponding to a degree of sensitivity of a tumor to treatment with an agent that inhibits the biologic activity of RNA polymerase II, and if the level of c-Myc mRNA, the level of c-MYC protein, or the level of both c-Myc mRNA and c-MYC protein is greater than or equal to a level of c-Myc mRNA, a level of c-MYC protein, or a level of both c-Myc mRNA and c-MYC protein corresponding to a degree of sensitivity of the tumor to treatment with an agent that inhibits the biologic activity of RNA polymerase II, contacting the tumor with an agent that inhibits the biologic activity of RNA polymerase II, thereby treating the tumor. The tumor may comprise cells that over-amplify c-Myc mRNA. The tumor may comprise cells that over-express the c-Myc protein. Preferably, the tumor comprises a tumor of the pancreas. Preferably, the tumor comprise a tumor of the ovaries. Optionally, the method may comprise isolating the cell from the tumor. Optionally, the method may comprise determining the level of c-Myc mRNA, the level of c-MYC protein, or the level of both c-Myc mRNA and c-MYC protein A method for treating a tumor in a subject in need thereof comprises determining whether the level of c-Myc mRNA, the level of c-MYC protein, or the level of both c-Myc mRNA and c-MYC protein in the tumor is greater than or equal to a level of c-Myc mRNA, a level of c-MYC protein, or a level of both c-Myc mRNA and c-MYC protein corresponding to a degree of sensitivity of the tumor to treatment with an agent that inhibits the biologic activity of RNA polymerase II, and if the level of c-Myc mRNA, the level of c-MYC protein, or the level of both c-Myc mRNA and c-MYC protein in the tumor is greater than or equal to a level of c-Myc mRNA, a level of c-MYC protein, or a level of both c-Myc mRNA and c-MYC protein corresponding to a degree of sensitivity of the tumor to treatment with an agent that inhibits the biologic activity of RNA polymerase II, administering to the subject an agent that inhibits the biologic activity of RNA polymerase II in an amount effective to inhibit the biologic activity of RNA polymerase II, thereby treating the tumor. The tumor may comprise cells that over-amplify c-Myc mRNA. The tumor may comprise cells that over-express the c-Myc protein. Preferably, the tumor comprises a tumor of the pancreas, ovaries, stomach, or esophagus. Optionally, the method may comprise determining the level of c-Myc mRNA, the level of c-MYC protein, or the level of both c-Myc mRNA and c-MYC protein in the tumor. Optionally, the method may comprise isolating a cell from the tumor and determining the level of c-Myc mRNA, the level of c-MYC protein, or the level of both c-Myc mRNA and c-MYC protein in the cell.

In accordance with the methods, the agent to be administered or otherwise contacted with the tumor may inhibit the expression or the biologic activity of the excision repair cross-complementing rodent repair deficiency, complementation group 3 (ERCC3) protein. The agent may inhibit the transcription of the ERCC3 gene. The agent may inhibit the translation of ERCC3 mRNA. The agent may inhibit the biologic activity of the ERCC3 protein. The agent may inhibit the transcription of the c-Myc gene. The agent may inhibit the expression of the C-MYC protein. The agent may inhibit the interaction of the ERCC3 protein with the C-MYC protein. The agent may inhibit the KRAS-ERK-MYC signal cascade. The agent may induce degradation of RNA polymerase II. The agent may induce proteasome degradation of RNA polymerase II. The agent may comprise triptolide, an analog of triptolide, or a prodrug form of triptolide.

A method for screening a cancer patient for the likelihood of responding positively to an agent that inhibits the biologic activity of RNA polymerase II comprises determining the level of c-Myc mRNA, the level of c-MYC protein, or the level of both c-Myc mRNA and c-MYC protein from a cell isolated from the patient, entering the determined level into a system for determining the sensitivity of a tumor to RNA polymerase II inhibition, causing the processor of the system to compare the level determined from the patient with the system's reference values of a level of c-Myc mRNA, a level of c-MYC protein, or a level of both c-Myc mRNA and c-MYC protein corresponding to a degree of sensitivity of the tumor to treatment with an agent that inhibits the biologic activity of RNA polymerase II, and determining a RNA polymerase II inhibition sensitivity score from the comparison. The patient may have a tumor comprising cells that over-amplify c-Myc mRNA. The patient may have a tumor comprising cells that over-express the c-Myc protein. The patient may have a tumor of the pancreas, for example, a PDAC tumor. The patient may have a tumor of the ovaries. The patient may have a tumor of the stomach. The patient may have a tumor of the esophagus.

BRIEF DESCRIPTION OF THE DRAWINGS

FIG. 5A and FIG. 5B show that ERCC3 regulates growth and confers resistance to triptolide.

DETAILED DESCRIPTION OF THE INVENTION

Various terms relating to aspects of the present invention are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

Inhibiting includes, but is not limited to, interfering with, reducing, decreasing, blocking, preventing, delaying, inactivating, desensitizing, stopping, knocking down (e.g., knockdown), and/or downregulating the biologic activity or expression of a protein or biochemical pathway.

The terms express, expressed, or expression of a nucleic acid molecule include the biosynthesis of a gene product. The term encompasses the transcription of a gene into RNA, the translation of RNA into a protein or polypeptide, and all naturally occurring post-transcriptional and post-translational modifications thereof.

The terms subject and patient are used interchangeably. A subject may be any animal, and preferably is a mammal. A mammalian subject may be a farm animal (e.g., sheep, horse, cow, pig), a companion animal (e.g., cat, dog), a rodent or laboratory animal (e.g., mouse, rat, rabbit), or a non-human primate (e.g., old world monkey, new world monkey). Human beings are highly preferred.

It has been observed in accordance with the invention that either or both of over-amplification of c-Myc mRNA and over-expression of C-MYC protein in a tumor correlates with sensitivity of the tumor to treatment with agents that inhibit RNA polymerase II, including triptolide. Using patient-derived xenograft mouse models of pancreatic and ovarian cancers with c-Myc gene amplification, sensitivity of tumors to triptolide was observed. In cases of high levels of c-Myc mRNA and high levels of c-MYC protein, treatment with triptolide produced complete tumor elimination and no regrowth in animals kept on a drug-free schedule from 30 to 60 days.

It was further observed that these tumor cells produced high level of non-phosphorylated c-Myc protein that was prone for degradation by the treatment with triptolide. It was observed that pancreatic cancer cells that carry multiple copies of the c-Myc gene and produce low or no phosphorylated c-MYC protein are oncogenically dependent on high levels of c-Myc for their survival. The established triptolide-resistant PDX models of c-Myc amplified pancreatic cancer revealed increased protection of c-Myc protein by phosphorylation at Serine 62 residue and also overexpression of ERCC3 protein, one of the established targets of triptolide with critical role in the RNA polymerase II driven transcription process.

Multiple PDX models of pancreatic and ovarian cancers with no c-Myc amplification also showed sensitivity to triptolide that was associated with significant tumor shrinkage, which followed by immediate regrowth after treatment cessation. Thus, it is believed that c-Myc amplification and/or overexpression may serve as a biomarker to stratify patients with wide range of cancers by their enhanced sensitivity to the treatment with triptolide, its analogues and prodrugs, and also agents that target RNA polymerase II driven transcription.

Accordingly, the invention features systems and methods for determining whether a cancer patient, especially an ovarian, pancreatic, gastric, or esophageal cancer patient, will respond positively to treatment with chemotherapeutic agents that inhibit the expression and/or biologic activity of RNA polymerase II, including transcription mediated by RNA polymerase II. The invention alters the normal course of a treatment modality through RNA polymerase II inhibition by providing a checkpoint insofar as the information about c-Myc mRA and protein levels in a tumor patient indicate whether or not that patient will appropriately respond to the RNA polymerase II inhibition therapy. In the case where the patient will not appropriately respond to RNA polymerase II inhibition therapy, for example, because that patient's c-Myc mRNA and/or protein levels are insufficiently elevated, the patient can be administered different treatment regimen that does not include RNA polymerase II inhibition. Any of the methods may be carried out in vivo, in vitro, or in situ.

In some aspects, a system comprises a data structure, which comprises reference values for levels of c-Myc mRNA, levels of c-MYC protein, or levels of both c-Myc mRNA and c-MYC protein that correspond to the sensitivity of a tumor to treatment with an agent that inhibits the biologic activity of RNA polymerase II. In tumors responsive to RNA polymerase II inhibition, levels of c-Myc mRNA and/or c-MYC protein are at least equal to, and in many cases are higher than a minimal threshold for RNA polymerase II inhibition to facilitate tumor cell death. For example, such a level may comprise a level that corresponds to the tumor being likely responsive to treatment with the agent (e.g., at or above the minimal threshold levels), and/or a level that corresponds to the tumor being likely unresponsive to treatment with the agent (e.g., below the minimal threshold levels). Responsiveness includes, for example, killing of cells in the tumor that come in contact with the agent. The levels of c-MYC protein may comprise levels for unphosphorylated c-MYC, and/or levels for c-MYC phosphorylated at the Serine 62 position.

The system also comprises a processor operably connected to the data structure. The processor may comprise a computer processor. The system may comprise a computer network connection, for example, an Internet connection. The processor may comprise various inputs and outputs.

Preferably, the processor is programmed to compare a level of c-Myc mRNA, a level of c-MYC protein, or a level of both c-Myc mRNA and c-MYC protein determined from a cancer patient with the reference values and/or levels of c-Myc mRNA, levels of c-Myc protein, or levels of both c-Myc mRNA and c-MYC protein in the data structure, and is also programmed to determine whether the tumor in the patient is sensitive, including the degree of sensitivity, or not sensitive to treatment an agent that inhibits the biologic activity of RNA polymerase II. For example, the processor may be programmed to determine a RNA polymerase II inhibition sensitivity score as a result of the comparison of the c-Myc mRNA and/or C-MYC protein levels in the patient with the reference value levels in the data structure. Thus, for example, once the level of c-Myc mRNA and/or c-MYC protein in the patient's tumor cells is determined, the level may be entered into the system, and the level may then be compared against the levels in the data structure, and if the patient levels are high enough, a likelihood of responsiveness of the tumor to treatment with RNA polymerase II inhibitors can be determined.

The processor may determine a RNA polymerase II inhibition sensitivity/response score based on the comparison of patient-sample c-Myc mRNA and/or C-MYC protein levels with the corresponding reference levels in the data structure. The determined response score may then be provided to a user, for example, a medical practitioner or the cancer patient. Accordingly, in some aspects, the system optionally comprises an output for providing the RNA polymerase II inhibition sensitivity/response score to a user.

The form of the RNA polymerase II inhibition sensitivity/response score is not critical, and may vary according to the needs of the practitioner or user of the system. In its simplest form, such a response score may be an indication whether the cancer patient, whose samples have been entered into the system for comparison against the data structure, will or will not respond positively to chemotherapy that targets RNA polymerase II for inhibition. A positive response includes, for example, a clinically significant killing of tumor cells, including a reduction in the size of the solid tumor, and including elimination of the tumor. A positive response may also include, for example, stabilizing the cancer such that no further growth occurs. At least a partial positive response may be considered a beneficial treatment outcome. A response score may comprise a scale of a likely positive response, for example, a scale of 1 to 10 or other suitable integers, with one end of the spectrum corresponding to a score that the patient likely will not respond positively to RNA polymerase II inhibition chemotherapy and the other end of the spectrum corresponding to a score that the patient likely will respond positively to RNA polymerase II inhibition chemotherapy. A response score may comprise a value indicative of a high likelihood of a positive response to RNA polymerase II inhibition chemotherapy, a value indicative of a moderate likelihood of a positive response to RNA polymerase II inhibition chemotherapy, or a value indicative of a low likelihood of a positive response to RNA polymerase II inhibition chemotherapy. In some aspects, a response score may be backed up by statistical significance, according to any suitable statistical methodology.

A response score may, for example, be a function of the level of c-Myc mRNA and/or the level of c-MYC protein in the patient's tumor cells. A response score may, for example, be a function of the type of chemotherapy, including the particular chemotherapeutic agent(s) or combinations thereof or dose thereof, or including the length of treatment or route of administration, among other factors that accompany the design and implementation of a particular chemotherapeutic regimen for a given patient. The agent may comprise triptolide, an analog of triptolide, a prodrug form of triptolide, or any combination thereof.

The particular agent(s) or combinations thereof preferably inhibit the biologic activity of RNA polymerase II, including transcription mediated by RNA polymerase II. In some aspects, the agent(s) or combinations thereof induce degradation of RNA polymerase II. Degradation may result from inhibition of the biologic activity, but degradation may also be a more direct function of the agent itself. RNA polymerase II degradation may comprise proteasome degradation. For example, the agent(s) or combinations thereof may induce proteasome degradation of RNA polymerase II. Thus, in some aspects the RNA polymerase II inhibition sensitivity score comprises a likelihood that the agent(s) or combinations thereof will inhibit the biologic activity of RNA polymerase II in the tumor, thereby treating the tumor. In some aspects, the RNA polymerase II inhibition sensitivity score comprises a likelihood that the agent(s) or combinations thereof will induce degradation of RNA polymerase II in the tumor, thereby treating the tumor. In some aspects, the RNA polymerase II inhibition sensitivity score comprises a likelihood that the agent(s) or combinations thereof will induce proteasome degradation of RNA polymerase II in the tumor, thereby treating the tumor.

In addition to or in the alternative to inhibiting the biologic activity of RNA polymerase II, the agent(s) or combinations thereof may inhibit the expression or the biologic activity of the excision repair cross-complementing rodent repair deficiency, complementation group 3 (ERCC3) protein. The agent(s) or combinations thereof may, for example, inhibit the transcription of the ERCC3 gene, or inhibit the translation of ERCC3 mRNA, or inhibit the biologic activity of the ERCC3 protein. Thus, in some aspects the RNA polymerase II inhibition sensitivity score comprises a likelihood that the agent(s) or combinations thereof will inhibit the biologic activity of ERCC3 in the tumor, including at the transcription, translation, or protein activity level, thereby treating the tumor.

In addition to or in the alternative to inhibiting the biologic activity of RNA polymerase II, the agent(s) or combinations thereof may inhibit the expression or the biologic activity of the c-MYC protein. The agent(s) or combinations thereof may, for example, inhibit the transcription of the c-Myc gene, or inhibit the translation of c-Myc mRNA, or inhibit the biologic activity of the C-MYC protein. Thus, in some aspects the RNA polymerase II inhibition sensitivity score comprises a likelihood that the agent(s) or combinations thereof will inhibit the biologic activity of c-MYC in the tumor, including at the transcription, translation, or protein activity level, thereby treating the tumor. In some aspects, agent(s) or combinations thereof may inhibit the interaction of the ERCC3 protein with the C-MYC protein. In some aspects, agent(s) or combinations thereof may inhibit the KRAS-ERK-MYC signal cascade.

In some aspects, the processor may be programmed to recommend a particular treatment regimen for the patient, based on the RNA polymerase II inhibition sensitivity score. For example, the processor may recommend for patients who are determined to have a strong likelihood of a positive response to be administered one or more agents that inhibit the biologic activity of RNA polymerase II. For example, the processor may recommend for patients who are determined to have a strong likelihood of a positive response to be administered a regimen of triptolide, an analog of triptolide, a prodrug form of triptolide, or any combination thereof. The chemotherapeutic regimen may be directed by a medical practitioner according to patient care standards known or suitable in the art.

Optionally, the system may comprise an input for entering c-Myc mRNA levels and/or C-MYC protein levels determined or otherwise obtained from patient samples into the system. Optionally, the system may comprise an output for providing results of a structure comparison, including a response score, to a user such as the subject, or a technician, or a medical practitioner.

The levels of c-Myc mRNA and/or levels of c-MYC protein in the data structure may comprise levels for particular tumor types, preferably for tumors that respond to RNA polymerase II inhibition if the levels are sufficient. The tumors may be any tumors that overamplify and/or overexpress c-MYC. The tumors may comprise pancreatic tumors. The tumors may comprise ovarian tumors. The tumors may comprise gastric tumors. The tumors may comprise esophageal tumors.

In some aspects, the system may comprise computer readable media comprising executable code for causing a programmable processor to compare a level of c-Myc mRNA and/or a level of c-MYC protein obtained from a cancer patient with levels of c-Myc mRNA, and/or levels of c-MYC protein that correspond to the sensitivity of a tumor to treatment with an agent that inhibits the biologic activity of RNA polymerase II, and for causing a programmable processor to determine a RNA polymerase II inhibition sensitivity score as a result of the comparison. The sensitivity score may be as described above, including a likelihood that the cancer patient will or will not respond positively to chemotherapy that targets RNA polymerase II for inhibition. Such computer readable media are also featured in accordance with the invention separate from the systems of the invention. The computer readable media may comprise a processor, which may be a computer processor.

In one aspect, the invention provides methods for determining whether a cancer patient may respond positively to inhibition of RNA polymerase II. In some aspects, the methods generally comprise the steps of comparing a level of c-Myc mRNA and/or level of c-MYC protein from a sample isolated from a cancer patient with levels of c-Myc mRNA and/or levels of c-MYC protein that correspond to the sensitivity of a tumor to treatment with an agent that inhibits the biologic activity of RNA polymerase II, and determining whether the patient will respond to chemotherapy that inhibits RNA polymerase II based on the comparison. The cancer patient may be a pancreatic cancer patient. The cancer patient may be an ovarian cancer patient. The sample isolated from the patient may comprise a cell isolated from a tumor in the patient.

The comparing step may be carried out, for example, using a processor programmed to compare patient levels of c-Myc mRNA and/or c-MYC protein with reference values of levels of c-Myc mRNA and/or c-MYC protein that correspond to the sensitivity of a tumor to treatment with an agent that inhibits the biologic activity of RNA polymerase II. The reference values may, for example, be present in a data structure. The determining step may be carried out, for example, using a processor programmed to determine whether a cancer patient will respond to RNA polymerase II inhibition, based on the comparison of patient samples with reference values. In some aspects, determining whether the patient will respond to RNA polymerase II inhibition comprises generating a RNA polymerase II inhibition sensitivity score as a result of the comparison. The response score may be as described above, including a likelihood that the patient will (at least partially) or will not respond positively to RNA polymerase II inhibition. Inhibition may be via triptolide, an analog of triptolide, a prodrug form of triptolide, or any combination thereof.

The systems, computer readable media, and platforms described or exemplified herein may be used in accordance with such methods. For example, the methods may comprise determining the level of c-Myc mRNA, the level of c-MYC protein, or the level of both c-Myc mRNA and c-MYC protein from a sample, such as a tumor cell, isolated from the patient, entering the determined level into a system as described or exemplified herein, causing the processor of the system to compare the determined level from the patient with a level of c-Myc mRNA, a level of c-MYC protein, or a level of both c-Myc mRNA and c-MYC protein in the data structure, with the data structure levels corresponding to a degree of sensitivity of the tumor to treatment with an agent that inhibits the biologic activity of RNA polymerase II, and causing the processor to determine a RNA polymerase II inhibition sensitivity score based on the comparison of patient and database levels of c-Myc mRNA and/or c-MYC protein.

In some aspects, in which the cancer patient is determined to have a likelihood of responding positively to RNA polymerase II inhibition therapy, the methods may further comprise the steps of treating the patient with an agent that inhibits the biologic activity of RNA polymerase II. Treating may include administering to the patient the agent in an amount effective to inhibit the biologic activity of RNA polymerase II.

The agent may comprise the plant *Tripterygium wilfordii* (the Thunder God Vine), or an extract thereof. The agent may comprise triptolide, an analog of triptolide, a prodrug form of triptolide, or any combination thereof. Triptolide may comprise the formula:

Triptolide analogs or prodrugs may comprise minnelide, or any molecule described in U.S. Pat. Nos. 6,548,537, 6,150, 539, or 7,863,464, or U.S. Publ. No. 2014/0107077, the entire contents of each of which are incorporated by reference herein. Administration may be according to any suitable route.

Thus, the invention also features methods for treating a tumor in a patient in need thereof. In some aspects, the methods comprise comparing the level of c-Myc mRNA and/or the level of c-MYC protein determined from a tissue sample isolated from the patient, for example, a cell or tissue isolated from the tumor, with reference values for a level of c-Myc mRNA and/or a level of c-MYC protein corresponding to a degree of sensitivity of a tumor to treatment with an agent that inhibits the biologic activity of RNA polymerase II and, based on the comparison, if the level of c-Myc mRNA and/or the level of c-MYC protein from the patient is greater than or equal to a level of c-Myc mRNA, a level of c-MYC protein, or a level of both c-Myc mRNA and c-MYC protein corresponding to a degree of sensitivity of the tumor to treatment with an agent that inhibits the biologic activity of RNA polymerase II, contacting the tumor with an agent that inhibits the biologic activity of RNA polymerase II, thereby treating the tumor.

In some aspects, the methods comprise determining whether the level of c-Myc mRNA and/or the level of c-MYC protein is greater than or equal to a level of c-Myc mRNA and/or a level of c-MYC protein corresponding to a degree of sensitivity of the tumor to treatment with an agent that inhibits the biologic activity of RNA polymerase II and, based on the determination, if the level of c-Myc mRNA and/or the level of c-MYC protein is greater than or equal to the level of c-Myc mRNA and/or the level of c-MYC protein corresponding to a degree of sensitivity of the tumor to treatment with an agent that inhibits the biologic activity of RNA polymerase II, administering to the subject an agent that inhibits the biologic activity of RNA polymerase II in an amount effective to inhibit the biologic activity of RNA polymerase II, thereby treating the tumor.

In any of the methods, the tumor may comprise cells that over-amplify c-Myc mRNA. The tumor may comprise cells that over-express the c-Myc protein. The tumor may comprise a pancreatic tumor, such as a PDAC tumor. The tumor may comprise an ovarian tumor. The tumor may comprise a gastric tumor. The tumor may comprise an esophageal tumor.

Contacting the tumor may comprise administering to the patient the agent in an amount effective to inhibit the biologic activity of RNA polymerase II. Administration may be according to any suitable administration modality, including, for example, oral administration or parenteral administration. The agent may inhibit the expression or the biologic activity of the ERCC3 protein. The agent may inhibit the transcription of the ERCC3 gene. The agent may inhibit the translation of ERCC3 mRNA. The agent may inhibit the biologic activity of the ERCC3 protein. The agent may inhibit the transcription of the c-Myc gene. The agent may inhibit the expression of the C-MYC protein. The agent may inhibit the interaction of the ERCC3 protein with the C-MYC protein. The agent may inhibit the KRAS-ERK-MYC signal cascade. The agent may induce degradation of RNA polymerase II. The agent may comprise triptolide, an analog of triptolide, a prodrug form of triptolide, or any combination thereof. Administration may be at the direction of a medical practitioner.

The effective amount of the agent may be tailored to the level of c-Myc amplification and/or the level of c-MYC overexpression. For example, in cases where c-Myc mRNA or c-MYC protein levels are high, less of the RNA polymerase II-inhibiting agent may be used, which may be particularly helpful for agents that have a high level of toxicity or a small therapeutic window. By way of example, by selecting patients with tumors that are particularly sensitive to triptolide, lower dosages of triptolide may be administered, with a decrease in side effects and improvement in the safety of the treatment.

The following examples are provided to describe the invention in greater detail. They are intended to illustrate, not to limit, the invention.

Example 1

Chemical Genomics Identified Transcription as a Target in PDAC

Through an IRB-approved protocol, patient-derived xenografts (PDX) and cell lines were derived from PDAC surgical samples. The technique of rapid expansion (5-6 passages) avoided artificial selection of 2D-adapted cell line subclones. Iterative chemosensitivity screens of reprogrammed PDAC cells from 6 patients were conducted using a focused library of 867 drugs (NCI Clinical Collection and the FDA-approved drug set). This moderate scale, fully-automated screen assessed tumor cell viability at 6 drug concentrations ranging from 16 nM-10 µM. Sixteen hits were identified (area under the curve (AUC) <1.0, 50% inhibitory concentration ($IC_{50}$)
<100 nM) that were highly cytotoxic in these 6 cell lines. Ten of these drugs directly inhibit gene transcription, and none have been previously considered for PDAC therapy: triptolide was the most potent among transcriptional repressors including actinomycin D, epirubicin (and other anthracyclin antibiotics), plicamycin.

Example 2

Targeting ERCC3 with Triptolide Shows Unprecedented Activity In Vivo

Figure 1A:
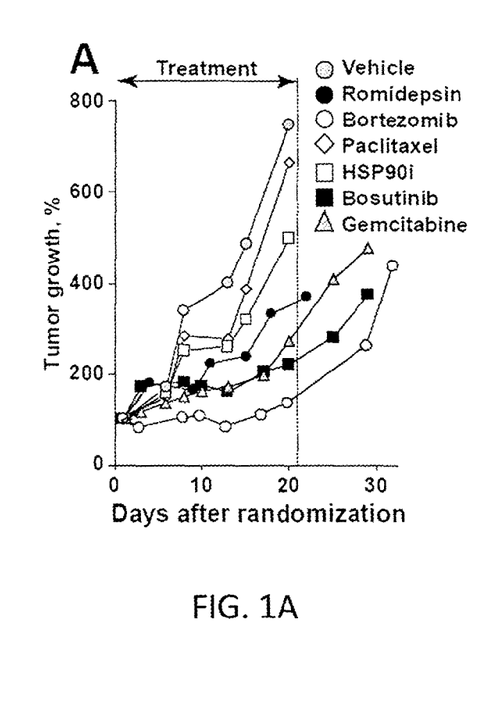
FIG. 1A shows patient-derived pancreatic cancer xenografts in mice treated for 21 days with various chemotherapeutic agents, with limited efficacy.
Figures 1B, 1C:
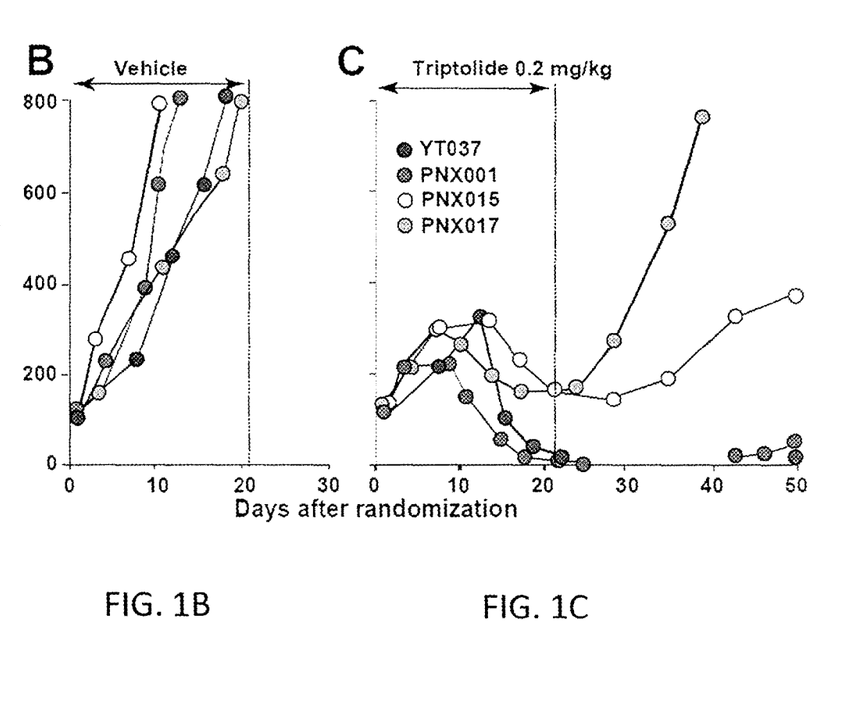
FIG. 1B shows robust control of the xenograft tumors in vivo (vehicle treated mice).
FIG. 1C shows complete regression of MYC-amplified pancreatic tumors (YT037 and PNX001) in mice after 21 days of treatment with triptolide. MYC-normal tumors (PNX015 and PNX017) showed only transient shrinkage after triptolide treatment. Each line is averaged volumes, n=5 mice/group.
Figure 2A:
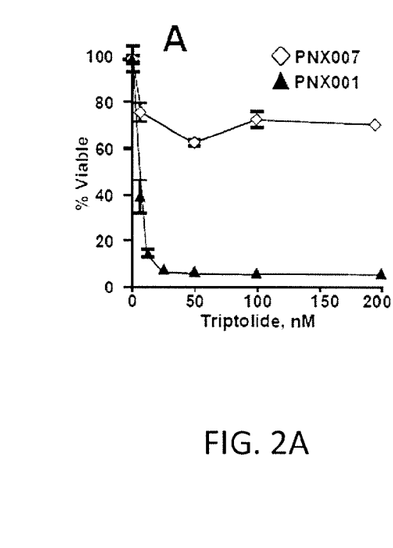
FIG. 2A shows differential sensitivity of re-programmed patient-derived PDAC cells to transcriptional inhibition with triptolide.

The screen hits were then validated in vitro and, selected drugs were directly tested on a genetically-characterized panel of PDAC PDX models. Treatment of pancreatic PDX with a wide range of clinically available compounds typically produces temporary growth delays (FIG. 1A). Extensive testing of one of the PDAC patient-derived xenografts, PNX001, revealed transient growth delay during the 21-day treatment trials of all tested agents, including a number of standard chemotherapies used in PDAC (FIG. 1A). It was determined that despite nearly identical growth rates of untreated patient-derived xenografts at F1-F3 passage (FIG. 1B), there was a dramatic difference in their sensitivity to triptolide (FIG. 1C, 2A): Two models, YT037 (dark grey circles) and PNX001 (middle grey circles), n=5 mice, 10 tumors in each group showed complete regression by the end of the 21-day treatment period. These mice remained tumor-free for at least 20 more days and exhibited no signs of toxicity. Genotyping of the PDAC reprogrammed cells and PDX models by high resolution comparative genome hybridization (CGH), and RNA and exome sequencing showed that all sources of tumor cells from patients PNX001 and YT037 showed MYC amplification in addition to mutations in KRAS and TP53.

Example 3

ERCC3 as Target of Interest for PDAC

Such unprecedented efficacy of triptolide in MYC-amplified PDX models prompted further investigation of the drug's effect on its transcriptional target, the RNA Pol II complex. Triptolide covalently binds to ERCC3, the xeroderma pigmentosum group B protein operating in the leading edge of the megadalton RNA Pol II complex as a helicase and a DNA translocase critical for promoter opening and promoter escape. MYC mRNA is one of the shortest-lived and ranks as the primary target of triptolide.

Figure 2B:
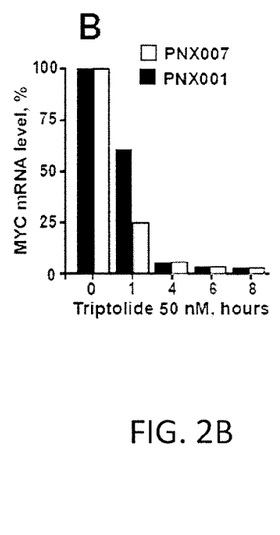
FIG. 2B shows rapid suppression of MYC mRNA in resistant and sensitive cells.
Figure 2C:
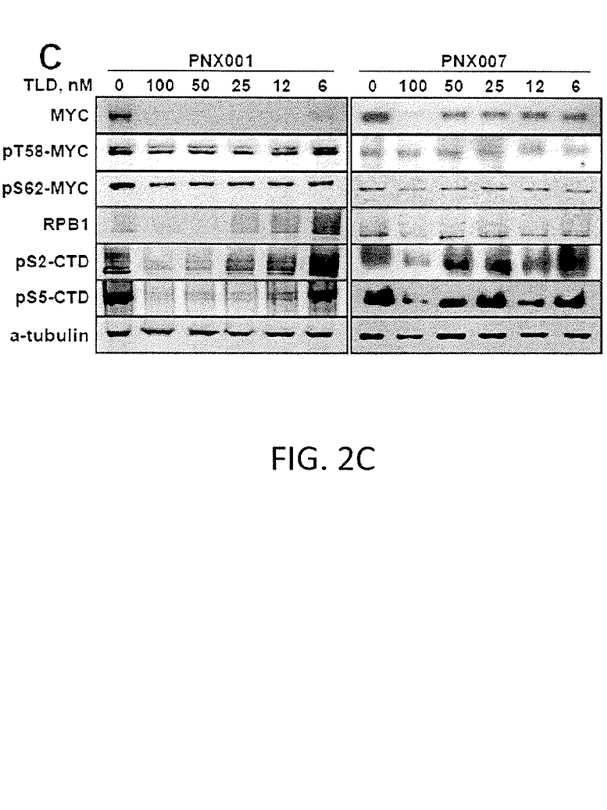
FIG. 2C shows persistence of p-MYC protein and high levels of RPB1-CTD phosphorylation in refractory PNX007, but not in sensitive PNX001 cells. Cells were treated overnight with triptolide, as indicated.

In both, sensitive PNX001 and refractory PNX007 cells (FIG. 2A), triptolide rapidly suppressed MYC transcripts (FIG. 2B). Contrastingly, triptolide-resistant PNX007 cells were insensitive to triptolide-induced MYC degradation (FIG. 2C). Of note, phosphorylated MYC proteins (FIG. 2C, pT58- and p562-MYC) resisted triptolide effects in both cell lines.

Figure 3A:
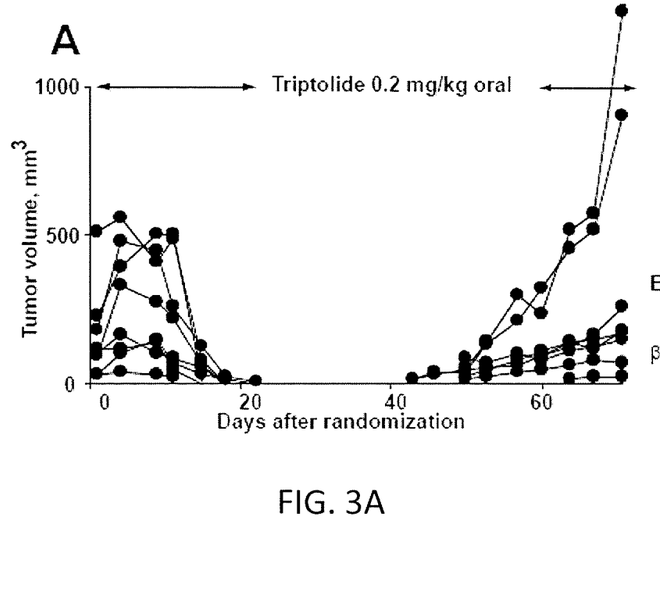
FIG. 3A shows resistance emergence after initial dramatic response of PNX001 to triptolide.
Figure 3B:
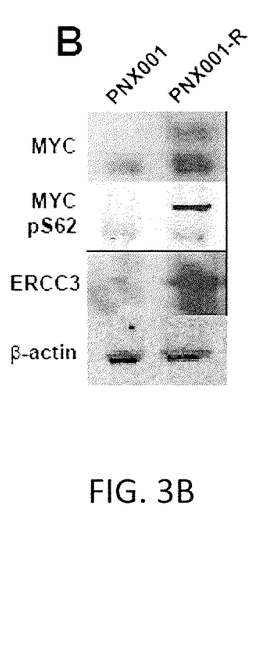
FIG. 3B shows resistant tumors have markedly increased pMYC and ERCC3.

Furthermore, pancreatic cancer PDX tumors that reappeared after complete regression (FIG. 3A), have acquired complete refractoriness to triptolide upon re-challenge. These tumors expressed markedly higher levels of phosphoS62-MYC and ERCC3 (FIG. 3B).

Figure 4A:
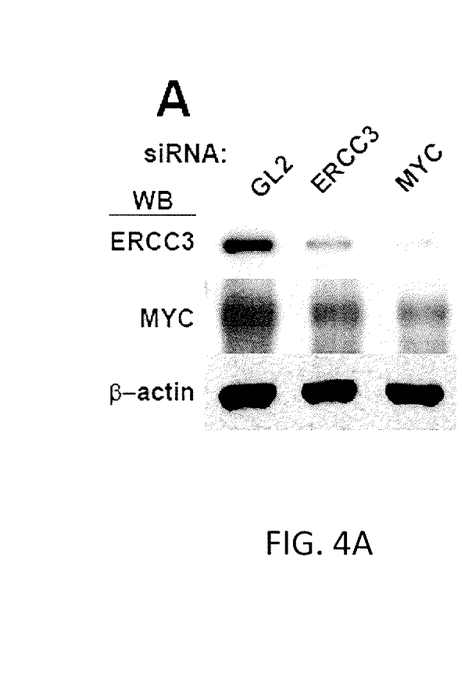
FIG. 4A shows interdependent MYC and ERCC3 protein levels 48 hours after siRNA silencing.
Figure 4B:
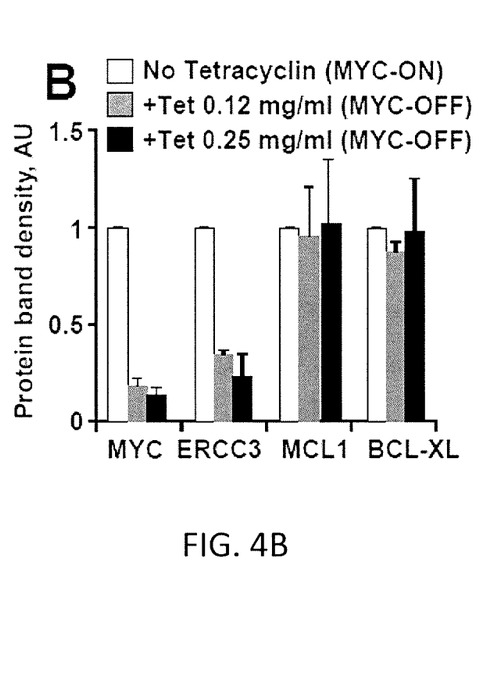
FIG. 4B shows repression with Tet in P493-6 cells regulates ERCC3.

The functional connection between MYC and ERCC3 is yet poorly understood. It was first established that ERCC3 siRNA markedly decreased MYC level on PNX001 cells (FIG. 4A). Conversely, MYC silencing dramatically depleted ERCC3 levels. This MYC-regulated expression of ERCC3 was further confirmed in P493-6 cells with Tet-repressor dependent expression of MYC (FIG. 4B). Without intending to be limited to any particular theory or mechanism of action, it is believed that ERCC3 blockade with siRNA or triptolide exerts its biological activity by deregulating short-lived mRNA including MYC.

These data suggest: 1) targeting transcription is highly active against PDAC; 2) MYC is one of the primary targets of ERCC3/triptolide and the driver of activated transcription in PDAC; 3) activity of KRAS-ERK-MYC axis stabilizes MYC protein and confers resistance to transcriptional inhibitors; hence, 4) combined targeting of transcription and KRAS-ERK pathway signaling may be synthetic lethal in PDAC.

Example 4

Basis for MYC-ERCC3 Interaction

The data (FIG. 3 and FIG. 4) show that ERCC3, as a critical part of RNA Pol II-TFIIH complex, is essential for MYC-mediated transcription of short-lived transcripts for genes regulating cell cycle, apoptosis and transcription itself. Multiple general transcriptional factors, but not ERCC3, have been previously identified in RNAi screen as synthetic lethal with MYC, suggesting the dependency of MYC-driven cancers on high transcription rate. It remains unclear, however, why ERCC3 was not identified as a synthetic lethal target.

Figure 5A:
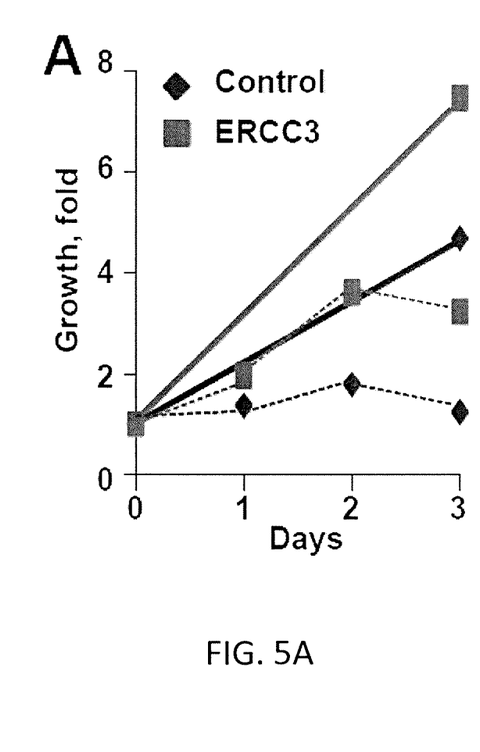
FIG. 5A shows HEK293 cells transfected with an ERCC3 cDNA expression construct grew faster (solid lines) and resisted triptolide (12.5 nM, dashed lines).
Figure 5B:
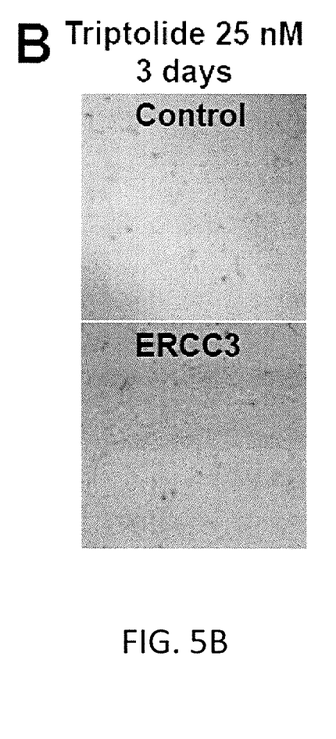
FIG. 5B shows a micrograph of HEK293 cells treated with triptolide 25 nM.

One possibility may be that triptolide uniquely inactivates ERCC3 molecule rendering it a dominant negative protein, and thus more effectively disabling MYC-driven RNA Pol II. The data indicate that increased expression of ERCC3 promotes cell growth (FIG. 5), and confers resistance to triptolide in a MYC-dependent manner (FIG. 3 and FIG. 5).

Ongoing and future studies will directly address the possible dominant negative mechanism for triptolide activity by overexpression of wild type and catalytically inactive ERCC3 mutants. Whether the triptolide differential activity in PDAC cell lines is due to varying levels of ERCC3 expression will be tested. The full-length ERCC3 and several truncated forms of ERCC3, including a catalytically inactive K346R-ERCC3 mutant, will be expressed to extend the experiments in HEK293 cells, (FIG. 5) in patient-derived early passage PDAC cells using lentiviral gene delivery (PNX001, YT037, PNX007, PNX017). The growth, tumorogenicity, and triptolide chemosensitivity of these modified cells will be determined. It is believed that the K346R-ERCC3 mutant mimics triptolide via a dominant negative effect. Expression of this mutant will be under the control of Tet-inducible promoter in the pHUSH vector. Using Gateway cloning and available panel of lentiviral expression constructs, a series of constitutive or Tet-regulated expression variants of ERCC3 will be generated in patient-derived pancreatic cancer lines. As an alternative approach, the levels of MYC or ERCC3 will be varied with shRNA to determine: i) dependency of ERCC3 expression on MYC levels; and ii) sensitivity to triptolide in relationship to MYC and ERCC3 expression.

Example 5

MYC Phosphorylation Via KRAS-MAPK Signaling as the Source of Resistance to Transcriptional Repressors Preliminary results support the hypothesis that resistance to transcriptional repressors is mediated via MYC stabilization: 1) phosphorylated protein species of MYC are relatively insensitive to arrest of transcription with triptolide (which inactivates ERCC3, FIG. 2C); 2) a subset of tumor cells that acquired resistance to triptolide exhibit highly elevated phospho-MYC and ERCC3 (FIG. 3); 3) MYC destabilization by MEK inhibitors induces rapid compensatory response from surface receptor signaling. Thus, it is believed that combined targeting of MYC with transcriptional repressors and destabilization of MYC by blockade of signaling may be highly effective against PDAC.

The effect on sensitivity to triptolide and other transcription inhibitors will be tested by introduction of degradation-resistant T58A-MYC to PNX001 cells that are highly sensitive to triptolide and actinomycin D. Lentiviral delivery and Gateway cloning will be used as described in Example 4. Expressing cells will be selected with puromycin or sorted by green fluorescence using GFP-containing pHUSH construct, and further validated by Western blotting. Cells induced to express T58A-MYC by addition of tetracycline to culture medium will be tested for sensitivity to triptolide and actinomycin D, or DNA-damaging chemotherapy (CPT11).

Example 6

Upstream Signaling Mechanisms Contributing to MYC Phosphorylation and Stabilization in Triptolide-Refractory PDAC Tumors MYC actively antagonizes the expression of a range of surface oncogenic receptor tyrosine kinases (RTK). MYC depletion releases this repressive mechanism and increases MAPK signaling which, in turn, stabilizes MYC. The RTK involved in activation of output from the KRAS-ERK-MYC axis in PDAC are yet unknown.

The patient-derived, tumor cell lines and triptoliderefractory PDX tumor tissue will be used to identify these activated pathways. Solid phase antibody arrays will be used.

Figure 6:
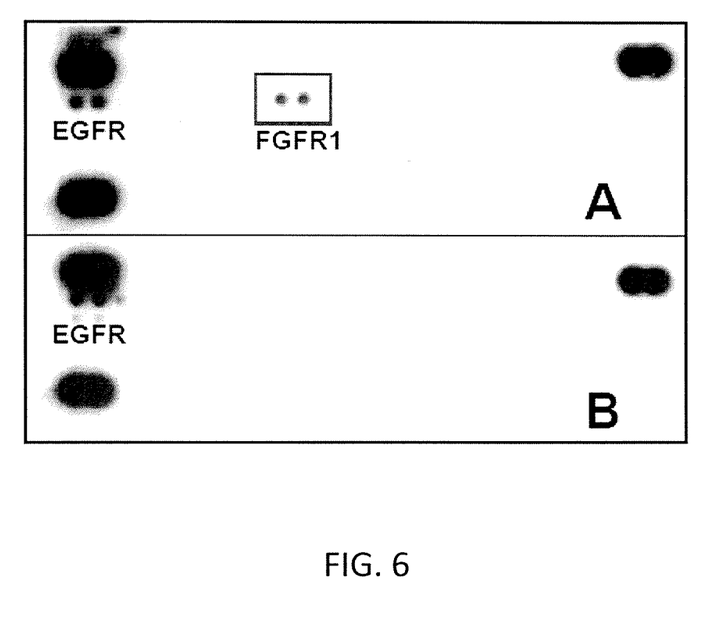
FIG. 6 shows an RTK array showing increased FGFR1 expression in PNX001 explants that acquired resistance to triptolide (panel A) compared to triptolide-sensitive samples (panel B).

Preliminary studies of triptolide-resistant PNX001 tumors demonstrated markedly increased FGFR1 expression in 2 out of 3 tumors tested (FIG. 6A). Comparative proteome profiling of the triptolide-resistant and sensitive tumors derived from PNX001, YT037, and from PDX tissues that exhibit primary resistance to triptolide (e.g. PNX007, PNX015) will be assessed. These PDX models have been already in vivo expanded, and cryopreserved for proteomics and re-implantation. It is believed that resistance to triptolide and other transcription inhibitors will be associated with accelerated signaling via RTK-KRAS pathway. These results will serve as the mechanistic basis for combination strategies aimed to disrupt MYC-stabilizing signaling.

Example 7

Inactivation of KRAS-ERK-MYC Signaling to Overcome Resistance to Transcriptional Inhibitors in PDAC Transcriptional repressors (triptolide, actinomycin D, anthracycline) will be tested in combination with FGFR, RAF, MEK, (e.g., AZD6244, PD184352), ERK, PI3K, AKT inhibitors, DNA-damaging (CPT11, platinum), protein destabilizing drugs (HSP90 inhibitor STA9090), BCL2 family inhibitors (ABT-199) in triptolide-refractory (PNX007, PNX015) and triptolide-sensitive (PNX001, YT037) cell lines. The in vitro-expanded PDAC cells will be systematically probed for synergy of pair-wise drug combinations (e.g., data in PNX001 cells with MEK and BCL inhibitors, Table 1, CI, coefficient of interaction). For statistical analysis, viability data will be formatted and processed in the R-package and assessed with the Chou-Talalay isobologram method (synergy defined as CI<<1). Synergistic combinations will be selected for future in vivo testing. In cases of drug-drug synergy, the effects of the combinations on MYC phosphorylation and stability will be assessed by Western blot.

TABLE 1

| Drug (Molar Ratio) | ED50 | ED75 | ED90 | Average CI | Interpretation |
|---|---|---|---|---|---|
| Triptolide/MEKi (1:6200) | 0.54 | 0.49 | 0.47 | 0.50 | Strong Synergy |
| Triptolide/BCLi (1:250) | 0.66 | 0.43 | 0.28 | 0.46 | Strong Synergy |

Example 8

Targeting of KRAS-ERK-MYC Signaling and Transcription Synergism In Vivo in PDX Models of PDAC It is desired to dismantle the KRAS-ERK-MYC axis in pancreatic cancer using rationally designed drug synergies. As a proof-of-concept experiment, a clinically proven MEK inhibitor, selumetinib/AZD6244, was selected to test for in vivo synergy with triptolide.

As the first step, the combination of triptolide and clinically available MEK inhibitor selumetinib/AZD6244 will be tested for synergism in vivo. Established triptolide-refractory PDX models will be used. In brief, 6-8 week old C.B17-SCID mice will be grafted in the flanks with cryopreserved PDAC tumor fragments soaked in Matrigel®. Animals (n=10 per group) will be randomized to receive triptolide 0.2 mg/kg, selumetinib 100 mg/kg administered orally twice daily 5 days per week for 3 weeks, a combination of two drugs or saline. Tumor volumes will be assessed twice a week as (length×width2)/2 for 6 weeks, and animals will be euthanized if tumor ulcerates or reaches 2000 mm$^3$. Tumor volume differences among groups will be analyzed using generalized linear models assuming appropriate family and link functions. Where necessary, models will be estimated using generalized estimating equations to account for correlated data.

To capture changes in KRAS-ERK-MYC signaling and in the expression of the surface RTKs, a separate cohort of dedicated xenografts will be collected either untreated or when refractory tumors recur following the initial response to triptolide (FIG. 3). Collected tumor tissues will be processed to obtain lysates (3 animals per group) and analyzed by commercial protein array with further validation by Western blot. Additional studies will determine if targeting FGFR1 or other RTKs in triptolide-resistant tumors (FIG. 6) synergizes with transcriptional repressors.

The invention is not limited to the embodiments described and exemplified above, but is capable of variation and modification within the scope of the appended claims.

We claim:

1. A method for treating a MYC-amplified tumor in a subject, comprising detecting overamplified levels of the c-Myc gene, overexpressed levels of c-MYC protein, or both overamplified levels of the c-Myc gene and overexpressed levels c-MYC protein in a cell isolated from the MYC-amplified tumor, determining that the serine at position 62 of the c-MYC protein is not phosphorylated, then administering to the subject an effective amount of triptolide or minnelide, an inhibitor of the excision repair cross complementing rodent repair deficiency, complementation group 3 (ERCC3) protein, thereby treating the MYC-amplified tumor, wherein the MYC-amplified tumor is pancreatic.

2. The method of claim 1, wherein the method comprises detecting overamplified levels of the c-Myc gene in the cell.

3. The method of claim 1, wherein the method comprises detecting overexpressed levels of c-MYC protein in the cell.

4. The method of claim 1, wherein triptolide is administered to the subject.

5. The method of claim 1, further comprising administering to the subject an effective amount of selumetinib.

* * * * *